United States Patent [19]
Kawata

[11] Patent Number: 5,908,295
[45] Date of Patent: Jun. 1, 1999

[54] DENTAL HANDPIECE WITH LIGHTING MEANS

[75] Inventor: Sosaku Kawata, Kanuma, Japan

[73] Assignee: Nakanishi Inc., Kanuma, Japan

[21] Appl. No.: 09/084,930

[22] Filed: May 28, 1998

[30] Foreign Application Priority Data

Jun. 9, 1997 [JP] Japan ................................. 9-150922

[51] Int. Cl.$^6$ ................................. A61C 1/00; A61C 3/00
[52] U.S. Cl. ................................. 433/29; 433/27; 433/132
[58] Field of Search ................................. 433/27, 29, 114, 433/126, 132

[56] References Cited

U.S. PATENT DOCUMENTS

| | | | |
|---|---|---|---|
| 4,230,453 | 10/1980 | Reimers | 433/29 |
| 4,680,011 | 7/1987 | Boinot | 433/29 |
| 4,723,911 | 2/1988 | Kurtz | 433/27 |
| 4,902,225 | 2/1990 | Lohn | 433/29 X |
| 5,800,172 | 9/1998 | Goldenberg | 433/29 X |

*Primary Examiner*—Nicholas D. Lucchesi
*Attorney, Agent, or Firm*—Keil & Weinkauf

[57] ABSTRACT

A dental handpiece is disclosed, which contains a handpiece body for giving dental treatment on a site in oral cavity of a patient, and an optical semiconductor device in the handpiece body for illuminating the site during the treatment. The optical semiconductor device is preferably LED, more preferably VLED.

8 Claims, 2 Drawing Sheets

DENTAL HANDPIECE WITH LIGHTING MEANS

FIELD OF THE INVENTION

The present invention relates to a dental handpiece, more specifically to a dental handpiece provided with lighting means for lighting up a treatment site in the oral cavity of a patient during treatment.

BACKGROUND ART

Some conventional dental handpieces are provided with lighting means for illuminating treatment site in the oral cavity of a patient during treatment. Light sources employed as such lighting means are predominantly high intensity halogen lamps.

FIG. 2 illustrates such a conventional handpiece 30 having turbine head 10' and a coupling 10". Halogen lamp 40 is disposed inside the coupling 10", and the light emitted by the lamp 40 is transmitted through a light transmitting fiber 42 such as rod fiber or glass fibers in the turbine head 10' to light projecting window 41 located in head 11 or neck 12 of the turbine head 10', which is to be positioned close to the treatment site in use, for illuminating the treatment site.

However, halogen lamp 40 has the following drawbacks:

(1) Halogen lamps employ filaments to generate light from electrical current passing therethrough. However, not a little portion of the electrical current is also converted to heat. Thus, the conversion efficiency from electric current to light is low, which increases consumption of electric power. In addition, the heated filaments endanger the safety of the handpiece.

(2) Filaments tend to rupture due to the rotational vibration caused by a micromotor in the dental handpiece or high speed rotation mechanism in an angle type handpiece, or due to cutting vibration generated in cutting the treatment site. Therefore, filaments in the halogen lamps have low shock resistance and thus short service life.

(3) The halogen lamps and the light transmitting fibers are not durable against steam when sterilized in an autoclave. Therefore, the lamps and the fibers require frequent replacement and repair, which causes unreasonably high cost.

(4) The halogen lamps cannot be disposed in the head or neck of the turbine head for direct illumination of the treatment site, since the size of the lamp cannot be decreased sufficiently for this arrangement. Accordingly, expensive light transmitting fibers should be used for light transmission, which makes the handpiece structure complex. Further, the light emitted by the halogen lamp attenuates physically through the light transmitting fibers by more than 20%.

In the field of display device, optical semiconductor device is often used as an optical display element due to its quick on-off response. Further, the optical semiconductor device is also used as a light source for various measurements. However, there has never been proposed to use an optical semiconductor device as lighting means in a dental handpiece.

DISCLOSURE OF THE INVENTION

It is an object of the present invention to provide a dental handpiece having lighting means in which electrical current is converted to light at high efficiency, which has high shock resistance, which has high resistance against steam when sterilized in an autoclave, and which is safe and durable.

It is another object of the present invention to provide a dental handpiece having lighting means with a simple structure in low cost.

According to the present invention, there is provided a dental handpiece comprising:

a handpiece body for giving dental treatment on a site in oral cavity of a patient, and an optical semiconductor device in said handpiece body for illuminating said site during the treatment.

PREFERRED EMBODIMENTS OF THE INVENTION

The present invention is now explained with reference to preferred embodiments taken in conjunction with attached drawings, but the present invention is not limited thereto.

Figure 1:
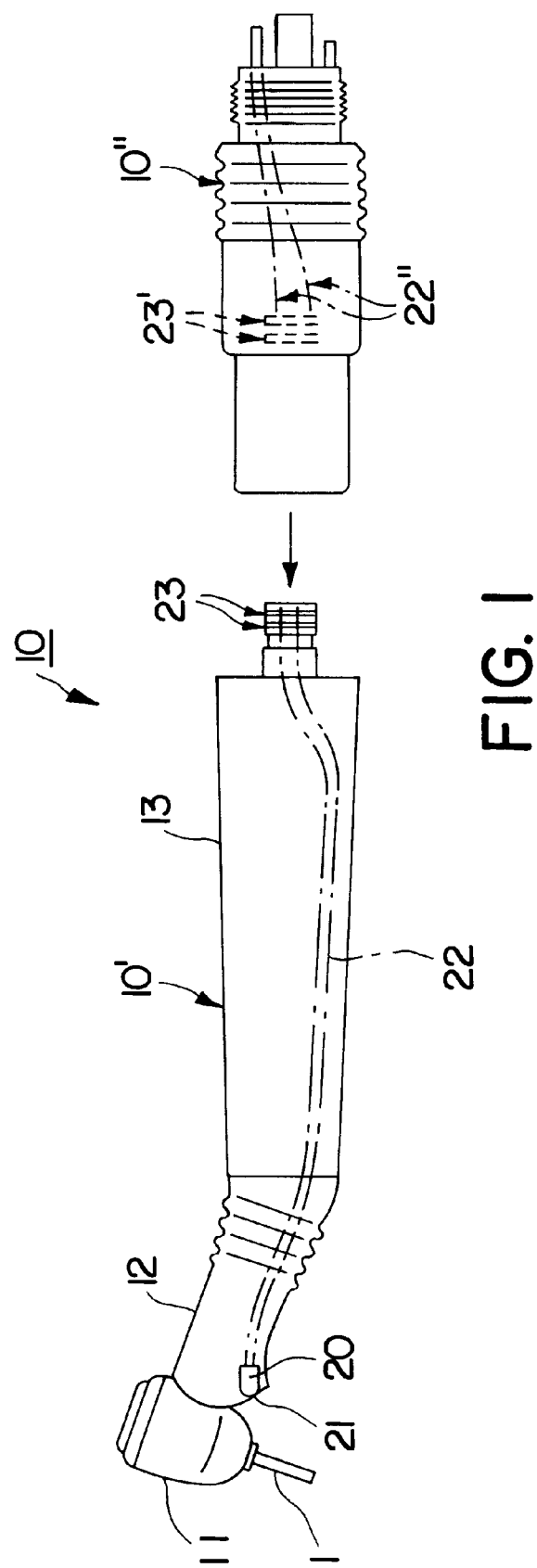
FIG. 1 is a partially exploded, schematic, perspective view of an embodiment of a dental handpiece of the present invention.
Figure 2:
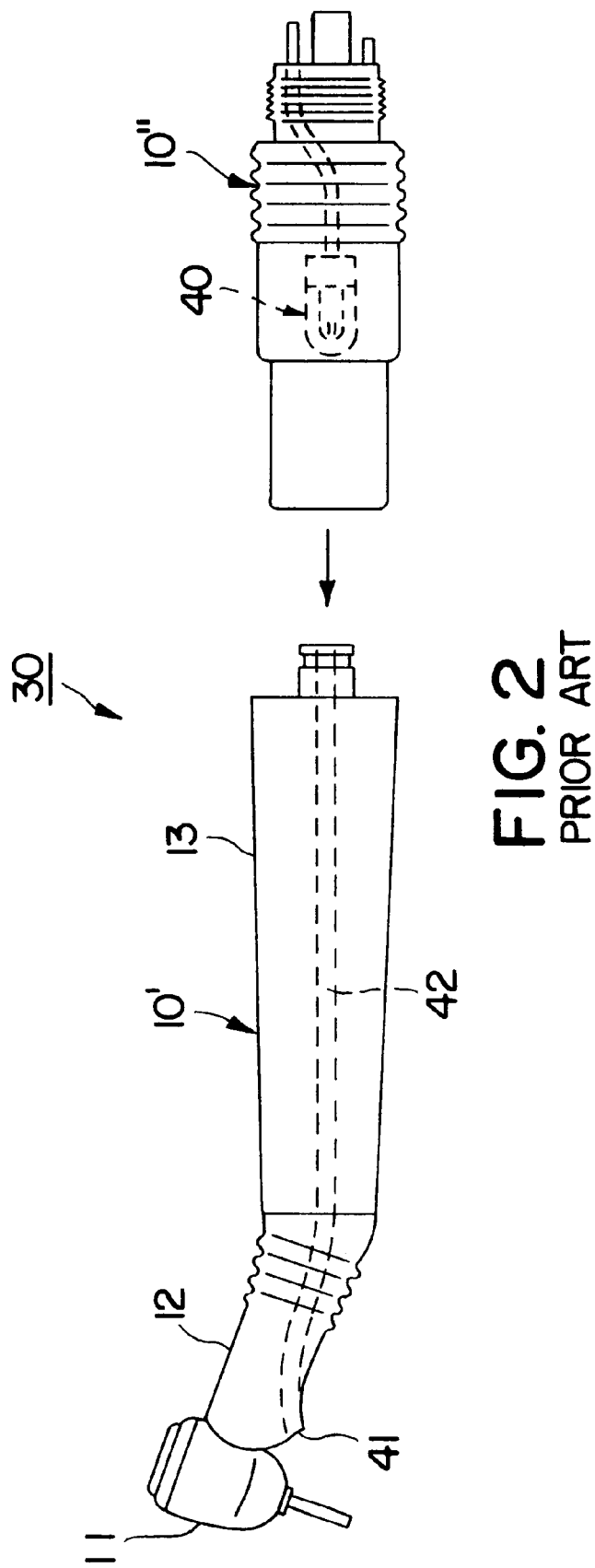
FIG. 2 is a partially exploded, schematic, perspective view of a conventional dental handpiece.

FIG. 1 shows dental handpiece body 10 of the present invention, which has been disassembled into turbine head 10' and coupling 10". The turbine head 10' is made up of head 11 to which a dental treatment tool 1 is detachably secured, neck 12 extending proximally from the head 11, and grip 13 arranged at an angle to the neck 12 and which is held by the operator during use of the handpiece 10. The coupling 10" connects the turbine head 10' to a dental hose (not shown), which is in turn connected to a dental unit (not shown), to provide connections for various fluid passages and electrical joints in the handpiece body 10.

In the present invention, optical semiconductor device is used as lighting means. The optical semiconductor device maybe a light emitting diode (LED) in particular a visible light-emitting diode (VLED).

In the present embodiment, VLED 20 is disposed in the lower distal portion of the neck 12 close to the head 11. VLED 20 is electrically connected to an external power supply (not shown). For example, VLED 20 is connected to lead wires 22 running through the turbine head 10' to contacts 23 at the proximal end of the turbine head 10'. Contacts 23 is in turn connected to contacts 23' in the coupling 10" to provide electrical connection between the turbine head 10' and the coupling 10". Contacts 23' is connected to leadwires 22' running through the coupling 10", which is then connected to the external power supply via a dental hose (not shown) In the lower distal end portion of the neck 12, light projection window 21 is provided in alignment with VLED 20 so that the light emitted by VLED 20 is directed toward the tip of the tool 1 to illuminate the treatment site in the oral cavity of a patient.

Although, in the present embodiment, VLED 20 is shown and described to be disposed in the neck 12 of the handpiece 10, the VLED 20 may alternatively be disposed in the head 11 of the handpiece 10. In that case, the light projection window 21 is provided on the head 11 in alignment with VLED 20 so that the illumination of the treatment site as described above may be achieved.

Further, VLED 20 may be disposed in the coupling 10", and the light emitted by VLED 20 may be transmitted through light transmitting means (not shown) such as optical fibers extending through the grip 13 and the neck 12 to the light projection window 21.

Since the dental handpiece of the present invention is provided with an optical semiconductor device as lighting means for illuminating the treatment site in the oral cavity of a patient, electric current is highly efficiently converted to light without employing filaments. Therefore, power consumption is reduced. For example, VLED 20 is operated at a low voltage of, for example, about 1.5 V to about 3 V, and at a low current of, for example, about 3 mA to about 50 mA. In addition, heat generation is substantially eliminated to ensure safety.

Further, elimination of filaments from the lighting means results in higher shock resistance and long service life of the lighting means. VLED is operative for, e.g., about not less than 100,000 hours.

Further, since the lighting means in the dental handpiece of the present invention is an optical semiconductor device, the size of the lighting means maybe reduced, so that the lighting means may be disposed in the head or neck of the handpiece for direct illumination of the treatment site in a preferred embodiment of the present invention. Accordingly, the necessity for expensive optical fibers such as rod fiber or glass fibers may be eliminated, and attenuation of the light is minimized. Further, the structure of the handpiece is simplified, and the cost is reduced.

Since the dental handpiece of the present invention does not use a halogen lamp having a filament, the handpiece has improved durability against steam when sterilized in an autoclave, and thus frequent replacement and repair of lighting means are not necessary. In addition, use of optical fibers may also be eliminated in a preferred embodiment of the present invention, which further improves durability of the handpiece.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

I claim:

1. A dental handpiece comprising a handpiece body for giving dental treatment on a site in oral cavity of a patient, said handpiece body including a turbine head having a neck and a coupling, and an optical semiconductor device in said neck of the handpiece body for illuminating said site during the treatment.

2. The dental handpiece as in claim 1 wherein said optical device is a light emitting diode (LED).

3. The dental handpiece as in claim 2 wherein said light emitting diode is a visible light emitting diode (VLED).

4. The dental handpiece as in claim 1 wherein said neck has a light project window in a distal portion of said neck, said window being in alignment with said optical device.

5. A dental handpiece comprising a handpiece body for giving dental treatment on a site in oral cavity of a patient, said handpiece body including a turbine head and a coupling; and an optical semiconductor device located in said coupling of the handpiece body for illuminating said site during treatment.

6. The dental handpiece as in claim 5 wherein said turbine head has a light projecting window in a distal portion of said turbine head, and wherein a light transmitting device extends through the turbine head to said window to transmit light from said optical device to said window.

7. The dental handpiece as in claim 5 wherein said optical device is a light emitting diode (LED).

8. The dental handpiece as in claim 7 wherein said light emitting diode is a visible light emitting diode (VLED).

* * * * *